United States Patent
Chou et al.

(10) Patent No.: US 12,007,355 B2
(45) Date of Patent: Jun. 11, 2024

(54) STRETCHABLE AND FLEXIBLE SENSING DEVICE

(71) Applicants: Kuan-Chien Chou, Taipei (TW); Boon-Ping Soh, Singapore (SG)

(72) Inventors: Kuan-Chien Chou, Taipei (TW); Boon-Ping Soh, Singapore (SG)

( * ) Notice: Subject to any disclaimer, the term of this patent is extended or adjusted under 35 U.S.C. 154(b) by 360 days.

(21) Appl. No.: 16/747,663

(22) Filed: Jan. 21, 2020

(65) Prior Publication Data
US 2020/0249197 A1    Aug. 6, 2020

Related U.S. Application Data

(60) Provisional application No. 62/799,077, filed on Jan. 31, 2019.

(51) Int. Cl.
*G01N 27/414* (2006.01)
*A61B 5/00* (2006.01)
(Continued)

(52) U.S. Cl.
CPC ....... *G01N 27/4146* (2013.01); *H05K 1/0283* (2013.01); *H05K 1/189* (2013.01);
(Continued)

(58) Field of Classification Search
CPC .. G01N 27/4146; H05K 1/0283; H05K 1/189; H05K 2201/05; H05K 1/0218; H05K 3/12; H05K 1/167; H05K 2201/10151; H05K 1/0277; H05K 1/028; H05K 1/0278; H05K 1/0281; A61B 5/02438; A61B 5/6804; A61B 2562/0261; A61B 5/28;
(Continued)

(56) References Cited

U.S. PATENT DOCUMENTS

| 11,150,114 B1 * | 10/2021 | Lagakos | G02B 6/4298 |
| 2007/0044571 A1 * | 3/2007 | Gysling | G01F 1/74 |
| | | | 73/861.18 |

(Continued)

FOREIGN PATENT DOCUMENTS

| CN | 110987246 A * | 4/2020 | G01L 1/142 |
| JP | 2017026396 A * | 2/2017 | |

(Continued)

OTHER PUBLICATIONS

Https://www.sciencedirect.com/topics/medicine-and-dentistry/polylactide#:~:text=Poly%20(I%2Dlactide)%20is,is%20approximately%2055%20%C2%B0C. (Year: 2015).*

*Primary Examiner* — Edward Chin
(74) *Attorney, Agent, or Firm* — McClure, Qualey & Rodack, LLP

(57) ABSTRACT

A stretchable and flexible sensing device includes a first elastic membrane, a first strain sensor and a processing unit. The first elastic membrane has a first surface, a second surface and a plurality of electrode contacts. The first surface and the second surface are disposed of opposite to each other and the electrode contacts are disposed on the first surface. One of the electrode contacts is as ground terminal. The first strain sensor is disposed on the first surface by printing technology so as to electrically connect to the electrode contacts. The processing unit is electrically connected to the electrode contacts. The processing unit operates according to a stretch resistance value of one of the first strain sensor.

16 Claims, 5 Drawing Sheets

(51) Int. Cl.
*A61B 5/024* (2006.01)
*H05K 1/02* (2006.01)
*H05K 1/18* (2006.01)

(52) U.S. Cl.
CPC ......... *A61B 5/02438* (2013.01); *A61B 5/6804* (2013.01); *H05K 2201/05* (2013.01)

(58) Field of Classification Search
CPC ....... A61B 5/296; A61B 5/297; A61B 5/1038; A61B 2562/12; A61B 5/6807
See application file for complete search history.

(56) References Cited

U.S. PATENT DOCUMENTS

| | | | | |
|---|---|---|---|---|
| 2014/0240932 A1* | 8/2014 | Hsu | ........................ | H05K 1/036 361/749 |
| 2017/0156636 A1* | 6/2017 | Kawamura | .............. | G01B 7/22 |
| 2018/0092206 A1* | 3/2018 | Iwase | .................... | H05K 1/0283 |
| 2018/0283844 A1* | 10/2018 | Kamakura | ................ | G01B 7/18 |
| 2018/0338544 A1* | 11/2018 | Huang | .................... | H05K 1/038 |
| 2019/0166688 A1* | 5/2019 | Iwase | ..................... | H05K 1/147 |
| 2019/0166689 A1* | 5/2019 | Iwase | ..................... | H05K 1/147 |
| 2019/0306972 A1* | 10/2019 | Baba | ........................ | G01B 7/22 |
| 2019/0343410 A1* | 11/2019 | Bahmanyar | ............ | A61B 5/686 |
| 2020/0085372 A1* | 3/2020 | Beamer | ................ | H05K 1/0283 |
| 2020/0225098 A1* | 7/2020 | Sun | ......................... | G01L 1/144 |
| 2020/0300718 A1* | 9/2020 | Bogdanovich | ....... | A61B 5/0002 |
| 2020/0390393 A1* | 12/2020 | Bruna | .................... | G01R 27/26 |
| 2021/0084768 A1* | 3/2021 | Higashira | ............ | H05K 1/0393 |

FOREIGN PATENT DOCUMENTS

| | | | | |
|---|---|---|---|---|
| WO | WO-2016144356 A1 * | 9/2016 | ......... | H01L 21/4853 |
| WO | WO-2018161152 A1 * | 9/2018 | ................ | A61B 5/00 |
| WO | WO-2018172701 A1 * | 9/2018 | ......... | A61B 5/02438 |

* cited by examiner

STRETCHABLE AND FLEXIBLE SENSING DEVICE

CROSS REFERENCE TO RELATED APPLICATIONS

This application claims the benefit of priority of Provisional Application Ser. No. 62/799,077, filed Jan. 31, 2019, the entire contents of which is incorporated herein by reference.

BACKGROUND OF THE INVENTION

Field of the Invention

The present invention relates to a sensing device, in particular, to a flexible sensing device for physiological state measurement.

Descriptions of the Related Art

The physiological status monitoring is one of the technologies that have been actively developed in recent years. After the combination of wearable devices, the early heart rate measurement has evolved to the blood pressure and blood oxygen measurement, which has been gradually applied in the general life of human beings, so as to achieve the purpose of early detection and early treatment through the real-time monitoring.

However, the wearable physiological status monitoring devices usually obtain the required data through a light source as the measurement basis. Such monitoring devices have a strong case, so they can only be made into the bracelets or neck rings and worn on the user. Thus, many applications are limited.

Therefore, it is one of the important subjects at present to provide a flexible sensing device that can enable the users to have better wearable experience and to expand the range of applications.

SUMMARY OF THE INVENTION

In view of the foregoing, the purpose of this invention is to provide a stretchable and flexible sensing device that can be easily combined with clothing or insoles and can reduce the user's foreign body sensation during the use.

To achieve the above, this invention is to provide a stretchable and flexible sensing device including a first elastic membrane, a first strain sensor and a processing unit. The first elastic membrane has a first surface, a second surface and a plurality of electrode contacts. The first surface and the second surface are set opposite to each other, and these electrode contacts are located on the first surface, and one of these electrode contacts is a ground terminal. The first strain sensor is arranged on the first surface of the first elastic membrane by printing technology and electrically connected to these electrode contacts respectively. The processing unit is electrically connected to these electrode contacts. The processing unit is to calculate and process according to the stretch resistance value of the first strain sensor.

In one embodiment, the stretchable and flexible sensing device further includes a second elastic membrane and an electromagnetic interference (EMI) prevention unit. The second elastic membrane is provided with a third surface and a fourth surface, and is bonded to the first surface of the first elastic membrane by the fourth surface. The EMI prevention unit is arranged on the third surface of the second elastic membrane and covers the relative position of the first strain sensor. In addition, the EMI prevention unit is electrically connected to the ground terminal of the first elastic membrane.

In one embodiment, the first elastic membrane and the second elastic membrane may be bonded by a liquid adhesive or a solid adhesive, or directly bonded by hot pressing.

In one embodiment, the stretchable and flexible sensing device further includes a flexible circuit board. The flexible circuit board is connected between the first elastic membrane and the second elastic membrane, to establish an electrical path between the EMI prevention unit and the ground terminal.

In one embodiment, the stretchable and flexible sensing device further includes a protective film, which is bonded with a third surface of second elastic membrane.

In one embodiment, the protective film and the second elastic membrane may be bonded by a liquid adhesive or a solid adhesive, or directly bonded by hot pressing.

In one embodiment, the first elastic membrane includes a first sub substrate and a second sub substrate, which are stacked, and the melting point of the first sub substrate is higher than that of the second sub substrate. The first strain sensor is arranged on the first sub substrate.

In one embodiment, the stretchable and flexible sensing device further includes a second strain sensor, which is arranged on the second sub substrate by printing technology and located between the first sub substrate and the second sub substrate. The arrangement of the first strain sensor and the second strain sensor is linear. In other embodiment, the arrangement of the first strain sensor and the second strain sensor can form a net.

In one embodiment, the first strain sensor is in a linear arrangement, and one end of each line is electrically connected to the ground terminal of the electrode contacts.

In one embodiment, the stretchable and flexible sensing device further includes a fixing component corresponding to the electrode contacts, and is threaded through the flexible circuit board to fix the processing unit, to electrically connect to the electrode contacts. The fixing component, for example, is a rubber ring, then the processing unit is fixed in the rubber ring.

In one embodiment, the material of the first strain sensor is selected from the polyvinylidene fluoride (PVDF), fluorinated trifluorinated polyethylene (PVDF-TrFE), carbon nanotubes, graphene ink, or silver nanoparticles ink.

In one embodiment, the first strain sensor includes a stretch resistance component.

As mentioned above, the stretchable and flexible sensing device of this invention uses a strain sensor capable of producing the changes in stretch resistance values as the main sensing component, and the strain sensor is arranged on an elastic membrane by printing technology, to make the sensing device flexible and stretchable. Accordingly, the stretchable and flexible sensing device of this invention can be combined with the objects that can touch the human skin, such as clothing or insole, for the pressure sensing or physiological semaphore measurement of human body.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DESCRIPTION OF THE PREFERRED EMBODIMENT

In the following description, this invention will be explained with reference to embodiments thereof. However, the description of these embodiments is only for purposes of illustration rather than limitation.

Figure 1:
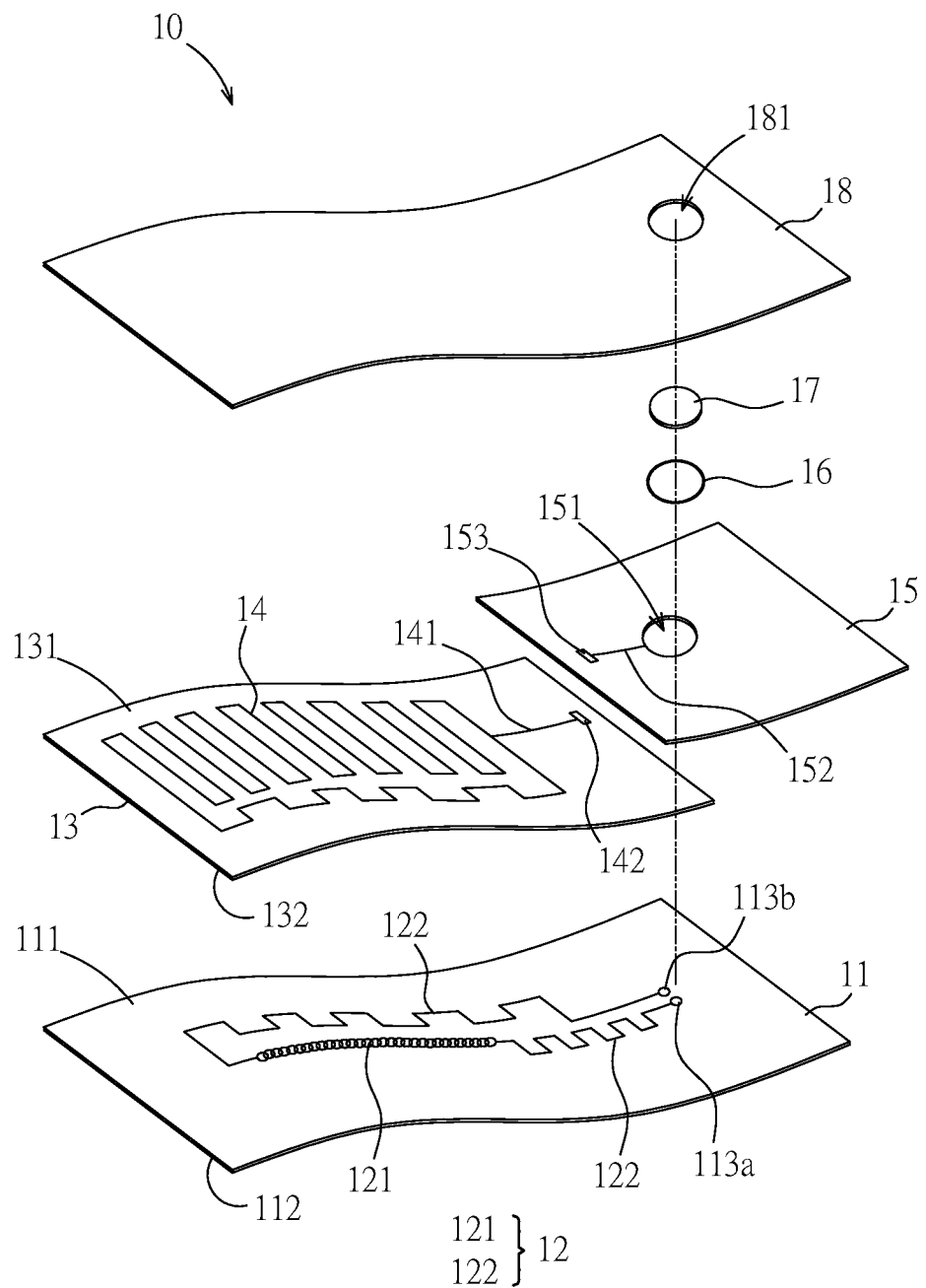
FIG. 1 is a decomposition diagram of the stretchable and flexible sensing device according to the first embodiment of this invention.
Figure 2:
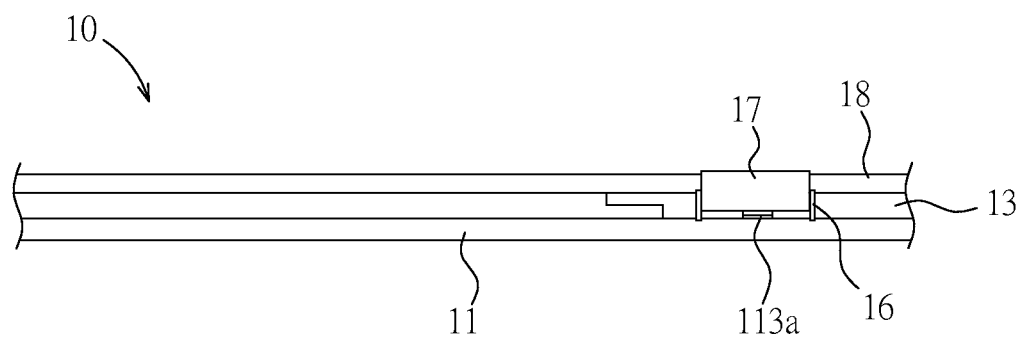
FIG. 2 is a side view of the stretchable and flexible sensing device shown in FIG. 1.

Please refer to FIG. 1 and FIG. 2, the stretchable and flexible sensing device 10 in the first embodiment of this invention includes a first elastic membrane 11, a first strain sensor 12, a second elastic membrane 13, an electromagnetic interference prevention unit 14, a flexible circuit board 15, a fixing component 16, a processing unit 17 and a protective film 18.

The first elastic membrane 11 has a first surface 111, a second surface 112 and two electrode contacts 113a-113b. The first surface 111 and the second surface 112 are arranged back-to-back. The electrode contacts 113a-113b are located on the first surface 111, wherein the electrode contact 113b is a ground terminal. In this embodiment, the material of the first elastic membrane 11 may be the thermoplastic polyurethane (TPU).

The first strain sensor 12 has a mutual electrically connected stretch resistance component 121 and a wire 122, which can be conveniently arranged on the first surface 111 of the first elastic membrane 11 by printing technology, and electrically connected to the electrode contacts 113a-113b respectively. The two ends of the stretch resistance component 121 are electrically connected to the electrode contacts 113a-113b through the wire 122. It should be noted that, the so-called stretch resistance component 121 is a component that produces the current or voltage changes during the tensile deformation, and its materials include but are not limited to the polyvinylidene fluoride, trifluorinated polyethylene, carbon nanotubes, graphene, or silver nanoparticles.

Figure 3A:
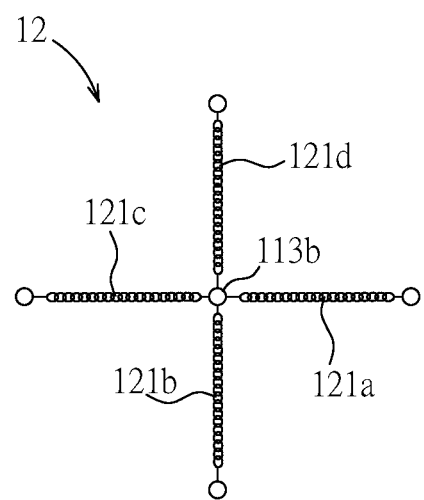
FIG. 3A and FIG. 3B are the schematic diagrams of the layout of the stretch resistance component of the first strain sensor.
Figure 3B:
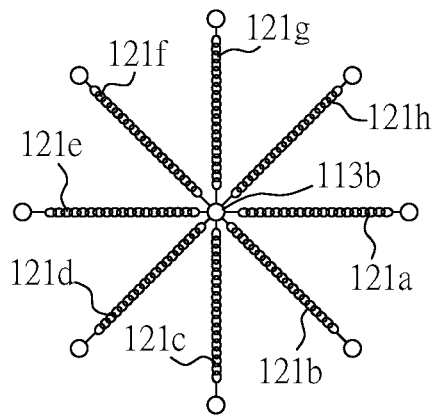

It is worth mentioning that the arrangement of the first strain sensor 12 on the first elastic membrane 11 is roughly linear. Furthermore, the main linear arrangement is the stretch resistance component 121. In addition, please refer to FIG. 3A again. The first strain sensor 12 can have a plurality of stretch resistance components 121a-121d, which are roughly arranged in a "cross" shape. One end of each stretch resistance component 121a-121d is electrically connected to the electrode contact 113b, which serves as the ground terminal. As shown in FIG. 3B, a plurality of stretch resistance components 121a-121h can also be arranged in the shape of "*". Since the stretch resistance component mainly changes its resistance value according to the tensile deformation and then changes the voltage and current, the arrangement of the stretch resistance component can be arranged according to the main deformation direction of the measured object.

The second elastic membrane 13 has a third surface 131 and a fourth surface 132, which are disposed opposite to each other. The second elastic membrane 13 is bonded to the first surface 111 of the first elastic membrane 11 through the fourth surface 132, so that the first strain sensor 12 is wrapped by the first elastic membrane 11 and the second elastic membrane 13. In this embodiment, the first elastic membrane 11 and the second elastic membrane 13 can be bonded by hot pressing technology, while in other embodiments, the first elastic membrane 11 and the second elastic membrane 13 can be bonded by the liquid or solid adhesive.

The EMI prevention unit 14 is arranged on the third surface 131 of the second elastic membrane 13, and electrically connected to the ground terminal of the first elastic membrane 11 through the wire 141 and electrical contact 142. Further, the location of the EMI prevention unit 14 on the second elastic membrane 13 corresponds approximately to the location of the first strain sensor 12, especially the location of the stretch resistance component 121. In addition, the EMI prevention unit 14 can be conveniently located on the third surface 131 of the second elastic membrane 13 through printing technology.

The flexible circuit board 15 has a hole 151, a wire 152 and an electrical contact 153. The flexible circuit board 15 is connected between the first elastic membrane 11 and the second elastic membrane 13, to establish a conductive path between the EMI prevention unit 14 and the electrode contact 113b, which serves as the ground terminal. The electrical contact 153 can electrically contact the electrical contact 142 of the EMI prevention unit 14. In addition, the position of hole 151 corresponds to the electrode contacts 113a~113b.

The fixing component 16 is arranged in the hole 151 of the flexible circuit board 15 to connect with the flexible circuit board 15. The fixing component 16 can be made of elastic materials, such as the rubber ring made of rubber, or of materials such as plastic, without limitation. In this embodiment, the inner surface of the fixing component 16 may have threads and may also have the electrical contacts extending from the wire 152 for electrical continuity.

The processing unit 17 is fixed in the fixing component 16 and electrically connected to the electrode contacts 113a-113b. The processing unit 17 is to calculate and process according to a stretch resistance value generated by the stretch resistance component 121 of the first strain sensor 12. In this embodiment, the processing unit 17 may perform the measurements of physiological signals including but not limited to the pressure, electrocardiogram (ECG), electrooculography (EOG), and electromyography (EMG), etc. In other embodiments, the sensed data calculation can also be uploaded by the processing unit 17 and executed through the cloud, not limited to be done by the processing unit 17. It is worth mentioning that the periphery of the processing unit 17 can also have threads corresponding to the threads of the fixing component 16, which can be combined with each other. Or even with proper structural design, the electrical conduction can be achieved at the junction of the processing unit 17 and fixing component 16.

The protective film 18 is engaged to the third surface 131 of the second elastic membrane 13, to cover the setting range of the EMI prevention unit 14. In addition, the protective film 18 has a hole 181 to expose the processing unit 17 at the junction with the second elastic membrane 13. The protective film 18 and the second elastic membrane 13 can be bonded directly by hot pressing, or by liquid or solid adhesive. In this embodiment, the material of the protective film 18 may be either thermoplastic polyurethane or UV-resistant material, which is not limited here.

Figure 4:
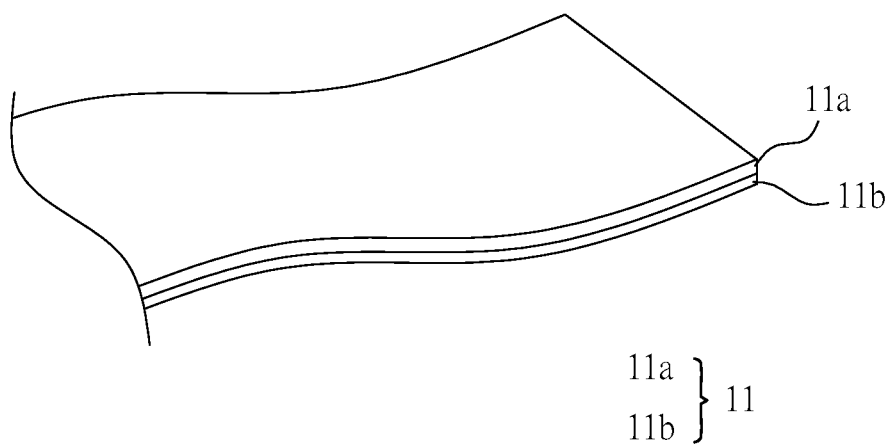
FIG. 4 is a schematic diagram showing the first elastic membrane composed of composite materials.

It is worth mentioning that the elastic membrane can also be composed of composite materials. Please refer to FIG. 4 again. Taking the first elastic membrane 11 as an embodiment, it can be formed by the in-mold injection of the stacked first sub substrate 11a and second sub substrate 11b. The melting point of the first sub substrate 11a is higher than that of the second sub substrate 11b, while the second sub substrate 11b with a lower melting point is suitable for the process of hot-pressing joint. In this embodiment, the elastic membrane formed by the composite material can also be applied to the second elastic membrane 13 or the protective film 18. As the embodiments are the same as above, no further details are given here.

Figure 5:
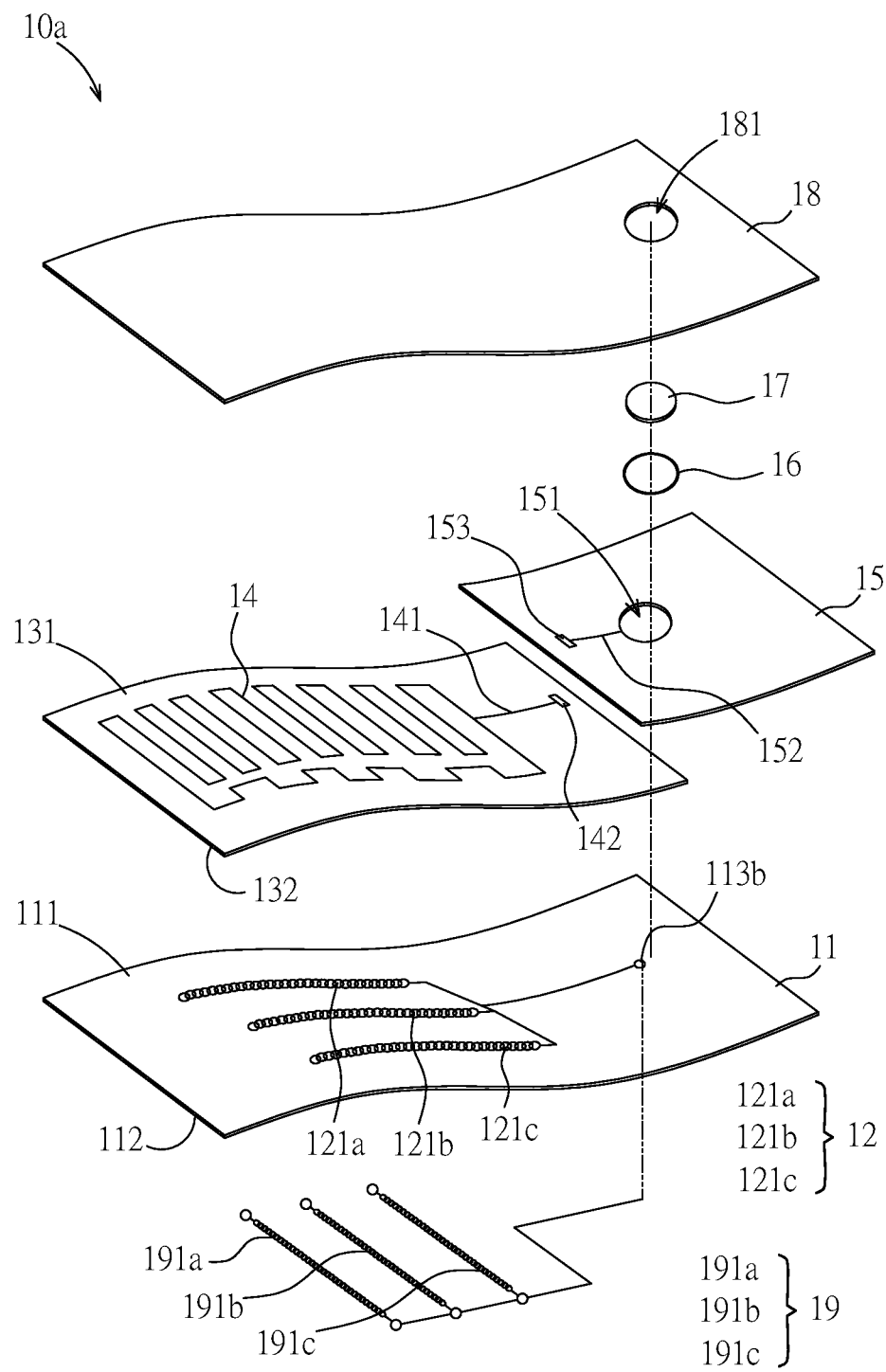
FIG. 5 is a decomposition diagram of the stretchable and flexible sensing device according to the second embodiment of this invention.

As shown in FIG. 5, the stretchable and flexible sensing device 10a disclosed in the second embodiment of this invention differs from the first embodiment in that the strain sensor is arranged differently, and the stretchable and flexible sensing device 10a of this embodiment also includes a second strain sensor 19.

As shown in FIG. 5, the second strain sensor 19 is set on the second surface 112 of the first elastic membrane 11. In this embodiment, the first strain sensor 12 has three stretch resistance components 121a-121c, while the second strain sensor 19 also has three stretch resistance components 191a-191c, and the relative relationship of the position is shown as a net when viewed from overhead. One end of each stretch resistance components 121a-121c and 191a-191c is mutual electrically connected to the electrode contact 113b, which serves as the ground terminal.

Although in this embodiment, the first strain sensor 12 and the second strain sensor 19 each have three stretch resistance components, the number of them can be adjusted according to actual needs, and not limited here.

Figure 6:
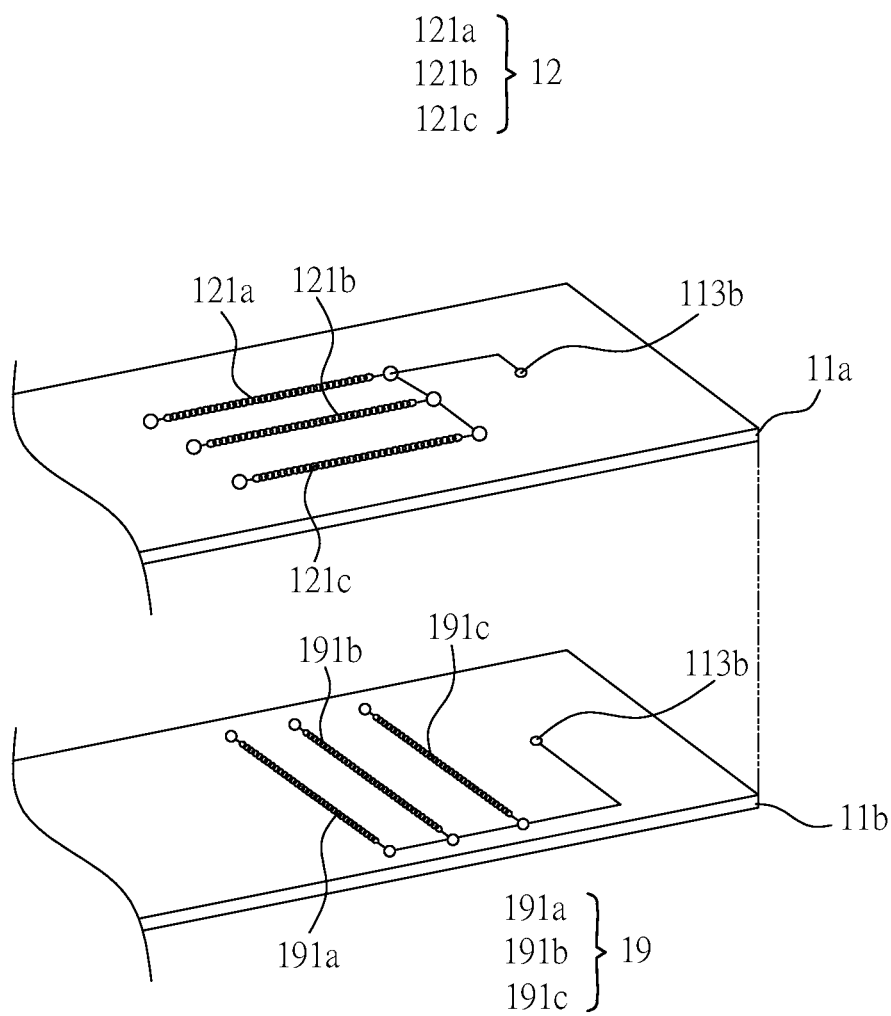
FIG. 6 is a schematic diagram of the second strain sensor arranged between the first sub substrate and the second sub substrate of the first elastic membrane.

In addition, as shown in FIG. 6, the second strain sensor 19 can also be arranged between the first sub substrate 11a and the second sub substrate 11b of the first elastic membrane 11, and the second strain sensor 19 can be protected through the second sub substrate 11b.

In conclusion, this invention discloses a stretchable and flexible sensing device which is a sensing component with a strain sensor capable of producing changes in the stretch resistance value, mainly as a strain sensor arranged on an elastic membrane by printing technology to make the sensing device flexible and extensible. Accordingly, the stretchable and flexible sensing device of this invention can be combined with the objects that can touch the human skin, such as clothing or insoles, by means of, for embodiment, hot pressing technology, to measure the human pressure or physiological state. In addition, part of the processing unit is embedded in the elastic membrane, which can make the flexible sensing device thinner, and can effectively reduce the foreign body sensation of the wearer.

The stretchable and flexible sensing device of this invention, if combined with an insole, can obtain the static and dynamic foot pressure or muscle extension state of the wearer through the data measured by the strain sensor, so as to determine whether the wearer has related diseases.

The above embodiments merely give the detailed technical contents of the present invention and inventive features thereof, and are not to limit the covered range of the present invention. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A stretchable and flexible sensing device, comprising:
a first elastic membrane, which has a first surface, a second surface and a plurality of electrode contacts, the first surface and the second surface are disposed opposite to each other, the electrode contacts are located on the first surface, one of the electrode contacts is a ground terminal, and the first elastic membrane is combined with an object by hot pressing that can wear on a human body and touch the human skin;
a first strain sensor, which is arranged on the first surface of the first elastic membrane by printing technology and electrically connected to the electrode contacts respectively, wherein the material of the first strain sensor is selected from the polyvinylidene fluoride (PVDF), fluorinated trifluorinated polyethylene (PVDF-TrFE), carbon nanotubes, graphene ink, or silver nanoparticles ink; and
a processing unit, which is electrically connected to the electrode contacts, and the processing unit is to calculate and process according to a stretch resistance value of the first strain sensor,
wherein the combination of the first elastic membrane and the first strain sensor is stretchable and flexible,
wherein the first elastic membrane comprises a first sub-substrate and a second sub-substrate, which are stacked, and the melting point of the first sub-substrate is higher than the melting point that of the second sub-substrate, and
wherein the second sub-substrate of the first elastic membrane is combined with the objects that can touch the human skin.

2. The stretchable and flexible sensing device of claim 1, further comprising:
a second elastic membrane, which has a third surface and a fourth surface are disposed opposite to each other, and is bonded to the first surface of the first elastic membrane by the fourth surface;
an electromagnetic interference prevention unit, which is disposed on the third surface of the second elastic membrane to electrically connected to the ground terminal of the first elastic membrane, and covers the relative position of the first strain sensor.

3. The stretchable and flexible sensing device of claim 2, wherein the first elastic membrane and the second elastic membrane is bonded by a liquid adhesive or a solid adhesive.

4. The stretchable and flexible sensing device of claim 2, wherein the first elastic membrane and the second elastic membrane is bonded by hot pressing.

5. The stretchable and flexible sensing device of claim 2, further comprising:
a flexible circuit board, which is connected between the first elastic membrane and the second elastic membrane, to establish an electrical path between the electromagnetic interference prevention unit and the ground terminal.

6. The stretchable and flexible sensing device of claim 5, further comprising:
   a fixing component, which is located corresponding to the electrode contacts, and is threaded through the flexible circuit board to fix the processing unit so as to electrically connect to the electrode contacts.

7. The stretchable and flexible sensing device of claim 6, wherein the fixing component is a rubber ring, and the processing unit is fixed in the rubber ring.

8. The stretchable and flexible sensing device of claim 2, further comprises a protective film, which is bonded with a third surface of the second elastic membrane.

9. The stretchable and flexible sensing device of claim 8, wherein the protective film and the second elastic membrane is bonded by a liquid adhesive or a solid adhesive.

10. The stretchable and flexible sensing device of claim 8, wherein the protective film and the second elastic membrane is bonded by hot pressing.

11. The stretchable and flexible sensing device of claim 1, wherein the first strain sensor is disposed on the first sub-substrate.

12. The stretchable and flexible sensing device of claim 11, further comprises a second strain sensor, which is located between the first sub-substrate and the second sub-substrate by printing technology.

13. The stretchable and flexible sensing device of claim 12, wherein the first strain sensor and the second strain sensor are in a linear arrangement, respectively.

14. The stretchable and flexible sensing device of claim 12, wherein the arrangement of the first strain sensor and the second strain sensor form a net.

15. The stretchable and flexible sensing device of claim 1, wherein the first strain sensor is in a linear arrangement, and one end of each line is electrically connected to the ground terminal of the electrode contacts.

16. The stretchable and flexible sensing device of claim 1, wherein the first strain sensor comprises a stretch resistance component.

* * * * *